United States Patent [19]

Merrill, Jr.; Alfred H. et al.

[11] Patent Number: 5,459,057
[45] Date of Patent: * Oct. 17, 1995

[54] METHOD OF MODIFYING CELLULAR DIFFERENTIATION AND FUNCTION AND COMPOSITIONS THEREFOR

[75] Inventors: Alfred H. Merrill, Jr., Stone Mountain; Joseph M. Kinkade, Jr., Decatur, both of Ga.; Victoria L. Stevens, Rahway, N.J.

[73] Assignee: Emory University, Atlanta, Ga.

[ * ] Notice: The portion of the term of this patent subsequent to Mar. 2, 2010 has been disclaimed.

[21] Appl. No.: 2,937

[22] Filed: Jan. 11, 1993

Related U.S. Application Data

[63] Continuation of Ser. No. 292,564, Dec. 27, 1988, Pat. No. 5,190,876.

[51] Int. Cl.$^6$ .............................. C12N 5/08; A61K 31/20; A61K 31/07
[52] U.S. Cl. ..................... 435/240.2; 514/559; 514/725
[58] Field of Search ............................... 435/240.1, 240.2, 435/240.26, 240.3; 564/507; 568/824; 514/559, 725

[56] References Cited

U.S. PATENT DOCUMENTS

| | | | |
|---|---|---|---|
| 4,342,828 | 8/1982 | Takaku et al. | 435/41 |
| 4,394,372 | 7/1983 | Taylor | 424/85 |
| 4,560,655 | 12/1985 | Baker | 435/241 |

OTHER PUBLICATIONS

Stevens, V. L. et al., Abstract of the 72nd Annual Meeting of the FASEB, Las Vegas, Nev., p. A1622 (May 1988).
Wilson, et al., Chem. Abstracts 105:24367z (1986).
Merrill, A. H. et al., Chem. Abstracts 105:169678z (1986).
Nelson, D. H. et al., Chem. Abstracts 105:91753y (1986).
Honma, Y. et al., Gann 73:97–104 (1982).
Koeffler, H. P. et al., Ciba Foundation Syposium 113:252–267 (1985).
Koeffler, H. P. et al., Blood 62(4):709–721 (1983).
Marx, J. L. et al., Science 236:778–779 (1987).
Breitman, T. R. et al., Proc. Natl. Acad. Sci. 77(5):2936–2940 (1980).
Strickland, S. et al., Cell 15:393–403 (1978).
Barnes, D., et al., Analytical Biochemistry 1022:255–270 (1980).
Ebeling, J. et al., Proc. Natl. Acad. Sci. 82:815–819 (1985).
Hesketh, J. E. et al., Bioscience Reports 6(9):797–804 (1986).
Hannun, Y. A. et al., J. Biol. Chem. 261:12604–12609 (1986).
Merrill, A. H. et al., J. Biol. Chem. 261:12610–12615 (1986).
Wilson, E. et al., J. Biol. Chem. 261:12616–12623 (1986).
Skubitz, K. M. et al., Blood 59(3):586–593 (1982).
Brandt, S. J. et al., Cancer Res. 41:4947–4951 (1981).
Imaizumi, M. et al., Blood 67(5):1273–1280 (1980).
Stevens et al., FASEB Journal 2, #7702 (1988).
Okazaki et al., Biological Abstracts 85(6):55569 (Mar. 1988).
Birnie, Br. J. Cancer 58(suppl.9):41–45 (1988).
Dalton et al., Blood 71:242–247 (1988).
Collins, Blood 70:1233–1244 (1987).
Imkaizumi et al., Eur. J. Haemoatol. 38:289–302 (1987).
Augeron et al., Cancer Research 44:3961–3969 (1984).
Lotan, Cancer Research 39:1014–1019 (1979).
Okazaki, Exp. Hematology 16:42–48 (1988).
Harris and Ralph, J. Leukocyte Biology 37:407–422 (1985).
Koeffler, Seminars in Hematology 223–236 (1986).
Francis et al., Leukemia Research 9:573–581 (1985).
Nakadate et al., Biochemical Pharmacology 37:1541–1545 (1988).

*Primary Examiner*—George C. Elliott
*Attorney, Agent, or Firm*—Needle & Rosenberg

[57] ABSTRACT

A method and composition for enhancing biological response modifiers, such as promoting cellular differentiation, by using a Vitamin A or an analog thereof and sphingosine or an analog thereof.

7 Claims, 3 Drawing Sheets

METHOD OF MODIFYING CELLULAR DIFFERENTIATION AND FUNCTION AND COMPOSITIONS THEREFOR

The United States government has rights in this invention pursuant to Grant Nos. GM33369 and CA22294, National Institute of Health. This application is a continuation of application Ser. No. 07/292,564, filed Dec. 27, 1988, now U.S. Pat. No. 5,170,876.

BACKGROUND OF THE INVENTION

The present invention relates to a method of effecting the modulation of differentiation of cells by serum factors and inhibitors of Protein Kinase C. More particularly, the present invention relates to the use of sphingosine and its analogs to promote cellular differentiation.

Differentiation is the modification of cells in structure or function during their course of development. Recent approaches to therapy for various types of cancer have focused on drugs that induce the maturation of the aberrant, differentiation-resistant cells causing the diseases. One example of such a compound is retinoic acid, which is a less toxic analog of vitamin A. Retinoic acid has been found to be a potent inducer of differentiation in established myeloid cell lines, as well as primary cultures of cells isolated from patients with promyelocytic leukemia.

However, a problem exists in that certain cellular functions can be controlled by biological response modifiers only under artificial conditions. It has been found that leukemic cells are less responsive in patients than when isolated from bone marrow and cultured in nutrient-rich medium supplemented with fetal calf serum. The success of retinoic acid therapy for a leukemia patient is typically predicted by determining the ability of the compound to induce differentiation of cells isolated from bone marrow and cultured in such medium. Clinical trials and case reports indicate that retinoic acid only induces differentiation in some patients and that the effectiveness of retinoic acid therapy is limited because many patients still develop infections to which they ultimately succumb. Furthermore, in many of the patients who do show improvement, the retinoic acid eventually ceases to cause differentiation and the leukemic cells proliferate.

There exists a need, therefore, for an improved method of controlling cellular differentiation and function using biological response modifiers.

There also exists a need for such a method which encourages differentiation under in-vivo conditions.

SUMMARY OF THE INVENTION

Protein Kinase C is an enzyme that participates in cellular responses to many serum factors. According to the present invention, the addition of an inhibitor of Protein Kinase C, such as sphingosine and its analogs, facilitates retinoic acid-induced differentiation. For example, it has been found that treating cells with both retinoic acid and sphinganine produce a more functional population of cells then those treated with retinoic acid alone.

The inhibitor can therefore be useful as an adjunct in the treatment of diseases in which the progression of the disease, or in which the therapy for the disease, involves growth factors, hormones, or a variety of drugs based on the mechanism of action of such compounds.

A specific example of the potential use of the present invention is the enhancement of leukemic cell differentiation in response to retinoic acid. The present invention may also be used in the treatment of cancer, arthritis, atherosclerosis, diabetes, inflammatory diseases, psoriasis, chronic granulomatous disease, and other diseases involving impaired function of cells in response to extra cellular stimuli.

It is an object of the present invention, therefore, to provide an improved method of controlling cellular differentiation and function using biological response modifiers.

It is also an object of the present invention to provide such a method which encourages differentiation under in-vivo conditions.

DETAILED DESCRIPTION OF THE INVENTION

The present invention relates to the use of an inhibitor of Protein Kinase C, such as sphingosine and its analogs, to enhance cell differentiation in response to other agents.

Figure 1:
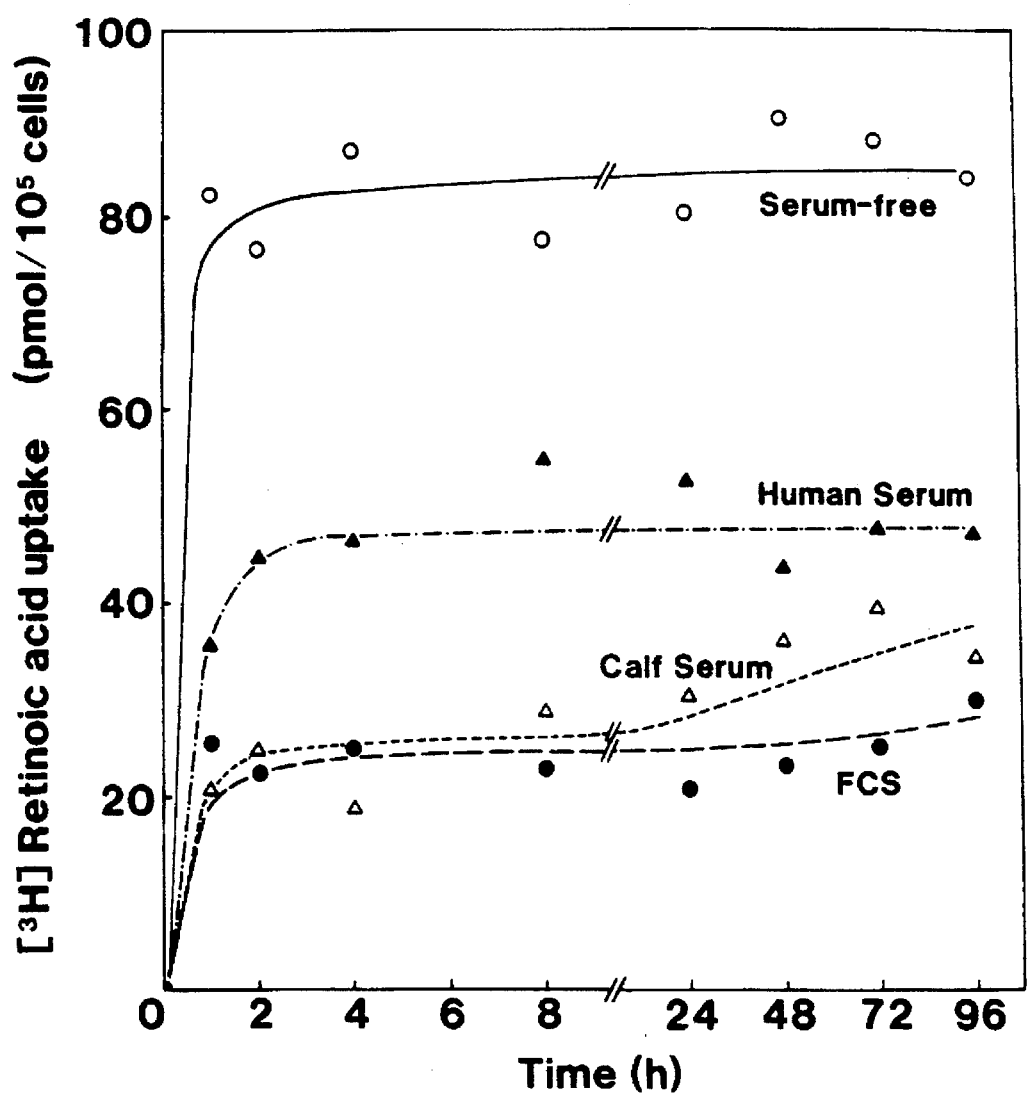
FIG. 1 summarizes the uptake of [$^3$H] retinoic acid by HL-60 cells.

The effects of different sera on RA-induced differentiation are shown in FIG. 1. The calls grown in serum-free medium show the most morphological (only 10% remained promyelocytic) as well as functional (82% ware NBT+) maturation after 4 days in RA. Serum has an inhibitory effect on differentiation by both criteria and varied with the source. FCS allows the most differentiation (25% remained promyelocytic and 58% were NBT+) while maturation in calf serum (HyClone, 43% were promyeloctyic and 43% NBT+), and human serum (44% were promyeloctic and 37% NBT+), was less. As is typically seen, a small percentage of the cells in each sera group exhibit a more differentiated phenotype without addition of RA.

It has been found that different retinoic acid-induced differentiation can be effected by sera. The effects of different sera on retinoic acid-induced differentiation of HL-60 cells are shown in Table I, below. HL-60 cells were originally isolated from a patient with acute myelocytic leukemia and can be induced to differentiate into either monocyte/macrophage-like cells upon treatment with pharbol esters or 1α,25-dihydroxyvitamine D$_3$ or granulocytes when placed in media containing retinoic acid.

HL-60 cells (between passages 20 and 30) were adapted to growth in the RPMI 1640 medium supplemented with no serum, fetal calf serum, human serum [type AB from male donors (Sigma)], or calf serum (all at 10% final concentration) and maintained by subculturing every 3 or 4 days at a density of 2.5×10$^5$ cells/ml. Differentiation was assessed after 4 of days growth in either the presence or absence of 1 uM RA (added from a 10 mM stock solution in DMSO to an initial cell number of 2.5×10$^5$ cells/ml) by morphology and nitro blue tetrazolium (NBT) reduction. Differentiation in response to retinoic and treatment was assessed by morphology (the percentage of the cellular population in the various stages of granulocytic differentiation) as well as functional assays (the activity of the NADPH oxidense as measured by the reduction of nitro blue tetrazolium (NBT) when activated by phorbol esters. Morphology was judged on slides prepared with a Shandon Southern cytospin stained with Wright-Giemsa stain (Camco Quik II). The results from a representative determination are also shown in Table I.

These findings have been confirmed by repeating the measurements twice for cells in serum-free medium and at least four times for those in serum-containing media. In each case, 200 cells were scored. The percentage of cells capable of reducing NBT was determined by counting the number which contained precipitated formazan after a 30 minute, 37° C. incubation with an equal volume of NBT (1 mg/ml in 140 mM NaCl, 9.2 mM $Na_2HPO_4$, 1.3 mM $NaH_2PO_4$, pH 7.4) and 160 nM phorbol 12-myristate 13-acetate. The percentages shown represent the average of three determinations in which at least 200 cells were counted. In Table I, Blast=myeloblast, Pro=promyeloctye, Myelo=myelocyte, Meta=meta=myelocyte, Band=banded neutrophil, and Seg= segmented neutrophil.

TABLE I

The results were as follows:

| Serum | [RA] | Blast | Pro | Myelo | Meta | Band | Seq | NBT+ |
|---|---|---|---|---|---|---|---|---|
| None | — | 0 | 86 | 10 | 4 | 0 | 0 | 17% |
|  | 1 uM | 0 | 10 | 33 | 33 | 14 | 10 | 82% |
| FCS | — | 0 | 88 | 6 | 2 | 1 | 3 | 7% |
|  | 1 uM | 0 | 25 | 33 | 25 | 9 | 8 | 58% |
| Calf | — | 0 | 87 | 11 | 1 | 1 | 0 | 6% |
|  | 1 uM | 1 | 43 | 31 | 17 | 8 | 8 | 43% |
| Human | — | 0 | 84 | 11 | 3 | 1 | 1 | 7% |
|  | 1 uM | 0 | 44 | 35 | 18 | 2 | 1 | 37% |

It was found, therefore, that cells grown in serum-free medium showed the most morphological and functional maturation after 4 days in retinoic acid. Serum had an inhibitory effect on differentiation by both criteria, and differentiation varied with the source. Fetal calf serum allowed the most differentiation while maturation in calf serum and human serum was less.

Figure 2:
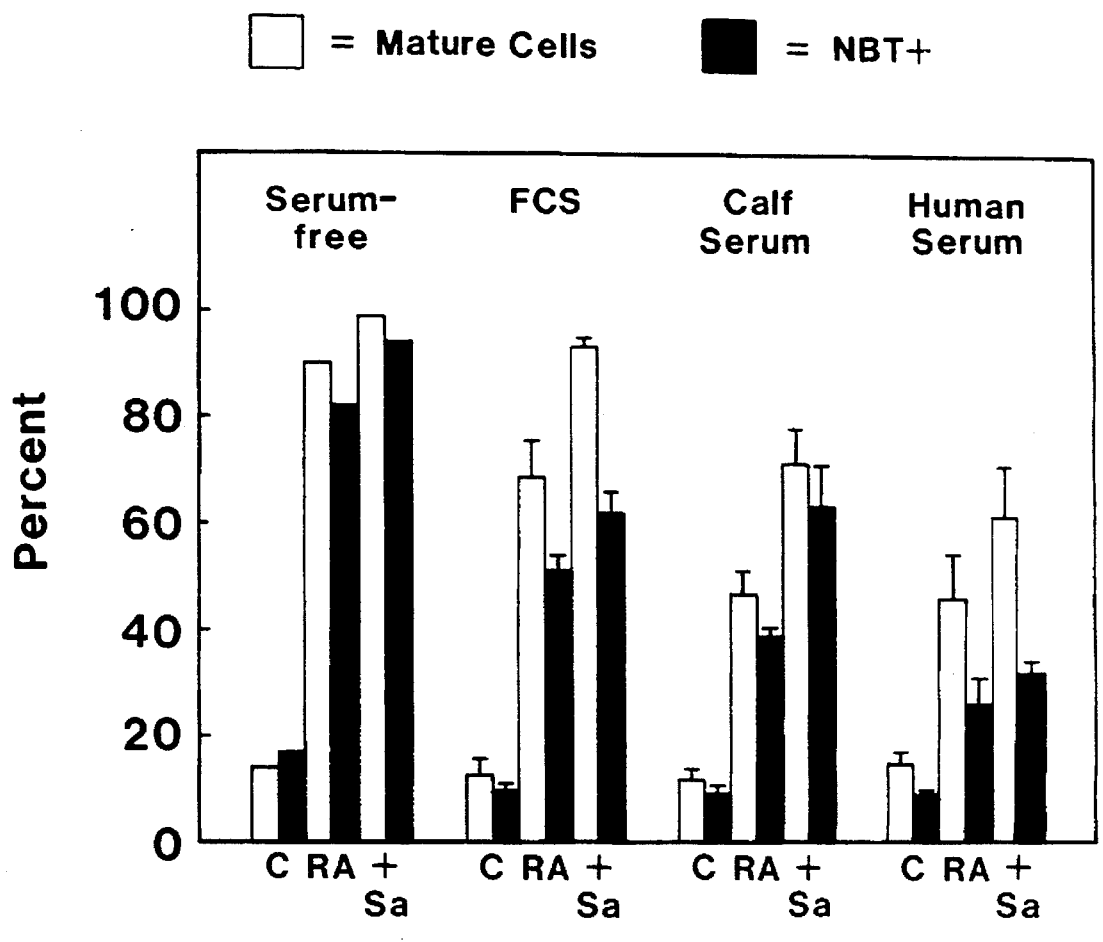
FIG. 2 summarizes the effect of sphinganine on retinoic acid-induced differentiation of HL-60 cells.

It has been determined that the enzyme Protein Kinase C plays an important role on the serum effects on retinoic acid-induced differentiation. It has also been found that sphinganine enhances retinoic acid-induced differentiation. Sphinganine, or 2D- or D-erythro-2- or (2S,3R)-2 amino, 1.3-octadecanediol, is a constituent of the sphingolipids and is known to be a potent inhibitor of Protein Kinase C. To determine the effects of sphinganine on retinoic acid-induced differentiation of HL-60 cells, 5×105 cells plated in 2 ml of RPMI 1640 medium containing the indicated serum (10%) in 12-well culture dishes (Costar) were treated with sphinganine (prepared as the 1:1 molar complex with bovine serum albumin as previously described) alone or in combination with 1 uM RA. The sphinganine was added daily to give the following final concentrations: serum-free, 1.0 uM/day; FCS, 2.5 uM/day; calf serum, 4.0 uM/day; human serum, 4.0 uM/day. The degree of maturity of each group was assessed by morphology (open bars, expressed as the percentage of cells which had matured beyond the promyelocyte stage) and NBT reduction (solid bars, determined as described above). The results for the serum-containing groups, reported as averages of at least 4 experiments shown ±S.E., are summarized in FIG. 2. In FIG. 2, C=control, RA=retinoic acid alone, and +Sa=retinoic acid plus sphinganine.

It was found that sphinganine had little effect on the retinoic acid-induced differentiation of HL-60 cells in serum-free medium; however, it increased the percentage of mature cells in all serum-containing media. The cells in fetal calf serum treated with retinoic acid and sphinganine differentiated to levels close to those seen with retinoic acid alone in serum-free medium (as judged by morphology). Likewise, the percentage of mature cells after retinoic acid and sphinganine treatment in calf serum was similar to those obtained with retinoic acid in FCS. The percentage of NBT positive cells was also increased although to a lesser extent. Treatment with sphinganine alone (i.e., without retinoic acid) also slightly increased the percentage of differentiated cells.

It has also been found that the initial rate of superoxide production in response to the chemotactic peptide N-formyl-L-methionyl-L-leucyl-L-phenylalanine (fMLP) can be increased with retinoic acid alone relative to indifferentiated cells. It was further found that the rate of fMLP-initiated respiratory burst was further increased by treatment with both retinoic acid and sphinganine.

During granulocytic maturation, cells normally acquire the ability to produce superoxide when activated by physiological stimuli such as the chemotactic peptide N-formyl-L-methionyl-L-leucyl-L-phenylalanine (fMLP) and phorbol 12-myristate 13-acetate (PMA). Whereas phorbol ester-stimulated superoxide production requires only a functional NADPH oxidase, the response to fMLP entails the presence of the fMLP receptor and the coupling mechanisms to the oxidase. HL-60 cells induced to differentiate by dimethylsulfoxide and dimethylformamide appear to develop all these components and produce superoxide when stimulated by fMLP, as reported by Skubitz et al., *Blood* 59,586 (1982) and Brandt et al. *Cancer Res.* 41,4947 (1981). However, cells treated with retinoic acid show little activation in response to this peptide, suggesting that maturation induced by this agent is incomplete. To determine whether sphinganine treatment affects the ability of retinoic acid-differentiated HL-60 cells to be activated by fMLP, the rate of superoxide production in response to both this peptide and PMA was quantitated.

Cells were grown in RPMI 1640 medium supplemented with 10% calf serum with no additions (control), 1 uM retinoic acid, 4.0 uM sphinganine (Sa, added on days 1 and 2 only), or both 1 uM retinoic acid and 4.0 uM sphinganine (added on days 1 and 2). After 4 days, the cells were collected by centrifugation and washed with phosphate buffered saline (PBS, 0.1 g/l $CaCl_2$, 0.2 g/l KCl, 0.2 g/l KH2PO4, 0.1 g/l $MgCl_2.6H_2O$, 8.0 g/l NaCl, and 2.16 g/l $Na_2HPO_4.7H_2O$) containing glucose (1 g/l). The cells were then resuspended in PBS+glucose at a density of $1\times10^7$ cells/ml. The respiratory burst of each group was quantitated by measuring the reduction of cytochrome c (25 mg/ml) as reflected by the change in absorbance at 549 nm minus 540 nm measured with a SLM Aminco DW-2000 spectrophotometer in the dual wavelength mode. Each measurement was done with $2.4\times10^6$ cells in a total volume of 2.4 ml. The respiratory burst shown in the top panel of FIG. 3 was initiated by fMLP (1 uM) while that in the lower panel was initiated with PMA (100 nM).

Figure 3:
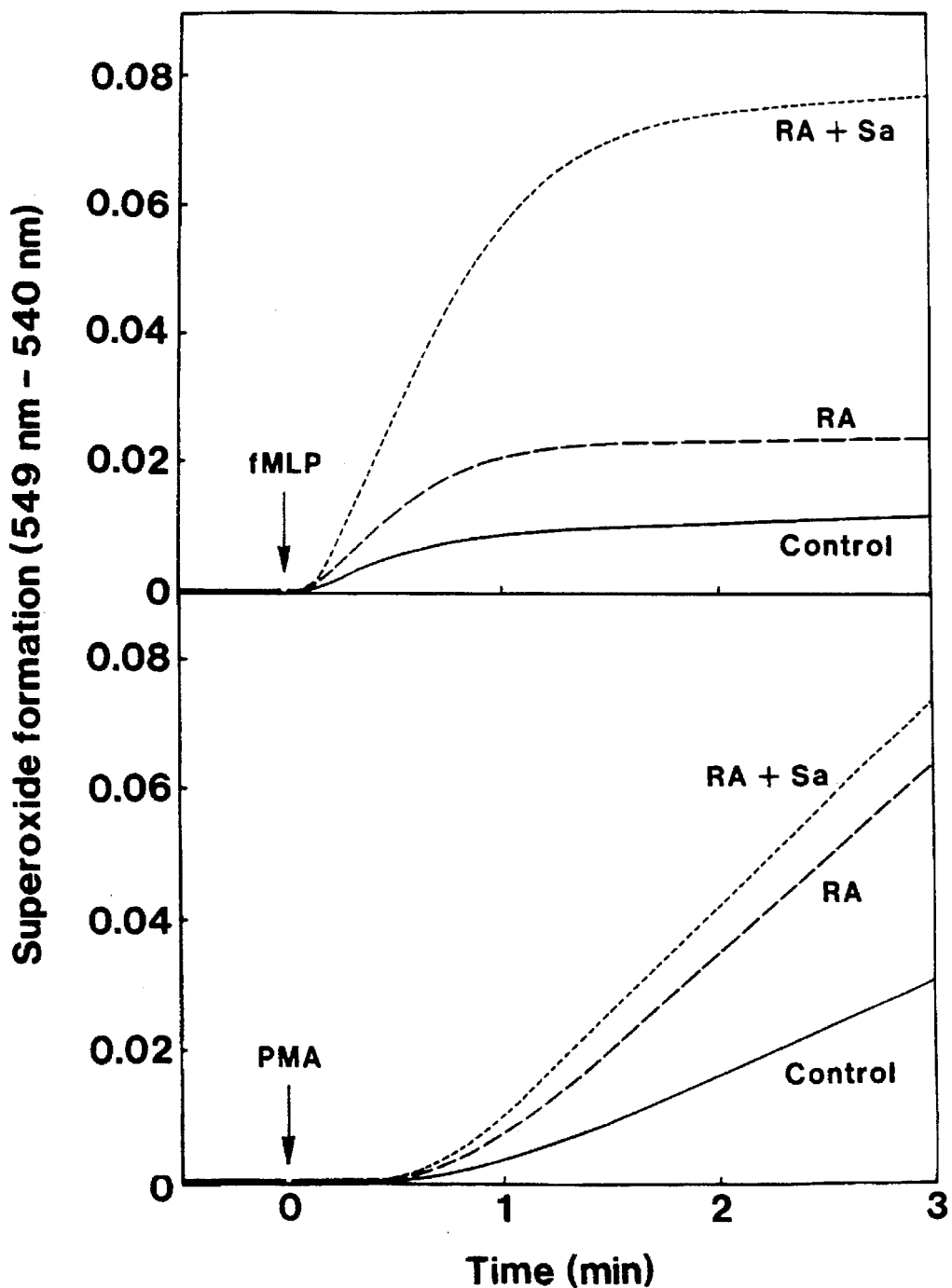
FIG. 3 illustrates the respiratory burst of differentiated HL-60 cells.

As summarized in FIG. 3, the response to fMLP in cells treated with retinoic acid alone increased by 220% relative to the undifferentiated cells, and the rate of respiratory burst was increased by 410% in HL-60 cells treated with both retinoic acid and sphinganine relative to the control. Some variability in the fMLP-stimulated rate of superoxide production was seen between different groups of cells: averages of results from 5 separate experiments show that this rate increased 75±30% for retinoic acid alone and 299±100% for retinoic acid plus sphinganine.

The rate of superoxide production in response to PMA was increased in cells differentiated with retinoic acid by 210% and with retinoic acid plus sphinganine by 230% both relative to the control rate in amounts consistent with the increases in NBT reduction above. The average increase, calculated from five experiments, was 82±24% for retinoic acid treated cells and 123±60% for cells treated with both retinoic acid and sphinganine. Therefore, because the increase in superoxide production when retinoic acid and sphinganine are used together is greater when stimulated by fMLP than by PMA, it appears that the long-chain base aids the HL-60 cells to differentiate more completely so that they become responsive to physiological agonists.

It has been found, therefore, that serum influences the ability of retinoic acid to induce cellular differentiation. Also, the addition of sphinganine has been found to not only increase the percentage of cellular population when differentiated, but also promotes more functional maturation of the cells. The use of sphingosine and its analogs as enhances of biological response modifiers provides means for overcoming the frequent failures of retinoic acid therapy, and provides differentiation under in-vivo conditions.

Furthermore, the present invention is not limited to retinoic acid, but applies to all systems with key processes that are inhibited by sphingosine and its analog and are involved in a biological process of interest.

For example, a daily intervenous dosage of approximately 50 mg and upt to 0.5 mg may be used, which compares to clinical studies of 13-cis-retinoic acid where doses of 50 to 100 mg per day are used.

What is claimed is:

1. A method of promoting cellular differentiation and maturity of myelocytic and promyelocytic cells capable of differentiation, as assessed by morphology or nitro blue tetrazolium reduction, comprising the step of treating said cells with an effective amount of sphingosine or an analog thereof.

2. The method of claim 1, wherein the analog of sphingosine is sphinganine.

3. A method of increasing superoxide production by granulocytes that are responsive to Vitamin A or an analog thereof, comprising the step of treating said granulocytes with effective amounts of Vitamin A or an analog thereof and sphingosine or an analog thereof.

4. The method of claim 3, wherein said analog of Vitamin A is retinoic acid.

5. The method of claim 3, wherein said analog of sphingosine is sphinganine.

6. The method of claim 3, wherein said superoxide production is in response to a chemotactic peptide.

7. The method of claim 6, wherein said chemotactic peptide is N-formyl-L-methionyl-L-leucyl-L-phenylalanine.

* * * * *